United States Patent
Basir et al.

(10) Patent No.: US 7,204,129 B2
(45) Date of Patent: Apr. 17, 2007

(54) REAL-TIME SYSTEM FOR DETECTING FOREIGN BODIES IN FOOD CONTAINERS USING ULTRASOUND

(75) Inventors: Otman Adam Basir, Kitchener (CA); Bosen Zhao, Guelph (CA); Gauri Mittal, Guelph (CA)

(73) Assignee: 1 M International Corporation, Waterloo (CA)

( * ) Notice: Subject to any disclaimer, the term of this patent is extended or adjusted under 35 U.S.C. 154(b) by 0 days.

(21) Appl. No.: 11/348,628

(22) Filed: Feb. 7, 2006

(65) Prior Publication Data

US 2006/0123911 A1    Jun. 15, 2006

Related U.S. Application Data

(62) Division of application No. 10/889,444, filed on Jul. 12, 2004, now Pat. No. 6,993,972, which is a division of application No. 10/263,383, filed on Oct. 2, 2002, now Pat. No. 6,782,752.

(60) Provisional application No. 60/326,547, filed on Oct. 2, 2001.

(51) Int. Cl.
  *G01N 11/00* (2006.01)
  *G01N 29/02* (2006.01)
(52) U.S. Cl. ............... 73/54.41; 73/54.01; 73/592
(58) Field of Classification Search ............... 73/54.41, 73/32 A, 54.01, 54.07, 54.13, 54.19, 64.42, 73/64.43, 61.79, 592
See application file for complete search history.

(56) References Cited

U.S. PATENT DOCUMENTS

| | | | |
|---|---|---|---|
| 2,427,319 A | | 9/1947 | Weathers |
| 3,969,926 A | * | 7/1976 | Walker et al. ............... 73/620 |
| 4,136,930 A | | 1/1979 | Gomm et al. |
| 4,651,568 A | * | 3/1987 | Reich et al. ............... 73/612 |
| 4,669,310 A | * | 6/1987 | Lester ............... 73/597 |

(Continued)

FOREIGN PATENT DOCUMENTS

DE    19940192 A1    3/2001

(Continued)

OTHER PUBLICATIONS

Malcolm J.W. Povey, Ultrasonics of food, Contemporary Physics, 1998, vol. 39, No. 6, pp. 467-478.

(Continued)

*Primary Examiner*—Helen Kwok
(74) *Attorney, Agent, or Firm*—Carlson, Gaskey & Olds, P.C.

(57) ABSTRACT

An ultrasound system determines the presence of a foreign object in a container of fluid by measuring echo signals from the outer surface of the container and the inner surface of the container. The amplitude of the echo signals are compared to determine the presence of an object in the container. The system also determines viscosity of the contained fluid by measuring a through-transmission time through the container and the fluid, measuring an outer echo transmission time of an outer echo signal from the outer surface of the container and an inner echo transmission time of an inner echo signal from the inner surface of the container, and determining a time difference between the outer echo transmission time and the inner surface transmission time.

5 Claims, 7 Drawing Sheets

U.S. PATENT DOCUMENTS

| | | | |
|---|---|---|---|
| 4,677,842 A * | 7/1987 | Piche | 73/32 A |
| 4,943,713 A | 7/1990 | Yoshida | |
| 5,038,615 A * | 8/1991 | Trulson et al. | 73/597 |
| 5,079,729 A * | 1/1992 | Nowakowski | 700/279 |
| 5,197,475 A * | 3/1993 | Antich et al. | 600/437 |
| 5,214,251 A * | 5/1993 | Orban et al. | 181/102 |
| 5,714,691 A * | 2/1998 | Hill | 73/861.04 |
| 6,182,511 B1 * | 2/2001 | Lucas | 73/630 |
| 6,227,040 B1 * | 5/2001 | Hastings et al. | 73/54.41 |
| 6,322,508 B1 * | 11/2001 | Goldenberg et al. | 600/443 |
| 6,378,357 B1 * | 4/2002 | Han et al. | 73/54.41 |
| 6,763,698 B2 * | 7/2004 | Greenwood | 73/30.01 |
| 6,912,891 B2 * | 7/2005 | Coupland et al. | 73/64.53 |

FOREIGN PATENT DOCUMENTS

| | | |
|---|---|---|
| EP | 0821230 A2 | 1/1998 |
| WO | WO 97/37217 | 10/1997 |

OTHER PUBLICATIONS

Edward Haeggstrom & Mauri Luukkala, Ultrasound detection and identification of foreign bodies in food products, Food Control 12 (2001) pp. 37-45, Helsinki, Finland.

T.H. Gan, D.A. Hutchins & D.R. Billson, Preliminary studies of a novel air-coupled ultrasonic inspection system for food containers, Journal of Food Engineering 53 (2002) pp. 315-323 Coventry United Kingdom.

Search Report PCT/CA02/01492, Oct. 2, 2002.

T.H. Gan., D.A. Hutchines, and D.R. Billson, "Preliminary studies of a novel air coupled ultasonic inspection system for food containers" Journal of Food Engineering, vol. 53, pp. 315-323 (2002).

E. Haeggestrom and M. Lukkala, "Ultrasound Detection and Identification of Foreign Bodies in Food Products", Food Control, vol. 12, p. 37 (2001).

R. Saggin, and J.N., Couplant described an ultrasonic reflectance coefficient method in "Ultrasonic characterization of oil viscosity and solids content" (2000 IFT Annual Meeting, Dallas, Texas, Jun. 11-14, 2000; 30D-11).

M.J. McCarthy, R.L. Powell, J.A. Fort, D.M. Pfund, and D.M. Sheen, "Development of ultrasonic Doppler velocimetry for viscosity measurements" (2000 IFT Annual Meeting. Dallas, Texas. Jun. 11-14, 2000. nr 49-6).

R. Saggin, J.N. Couplant, "Concentration measurement by acoustic reflectance," J Food Sci., vol. 66, pp. 681-685 (2001).

T.H. Gan., D.A. Hutchins & D.R. Billson, Preliminary studies of novel air-coupled ultrasonic inspection system for food containers, Journal of Food Engineering 53 (2002) pp. 315-323 Coventry United Kingdom.

\* cited by examiner

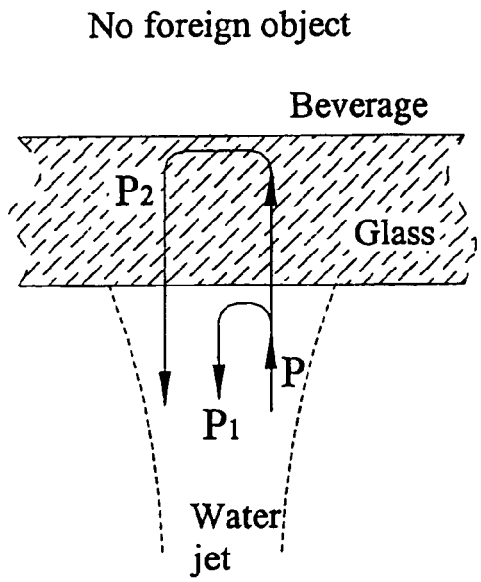
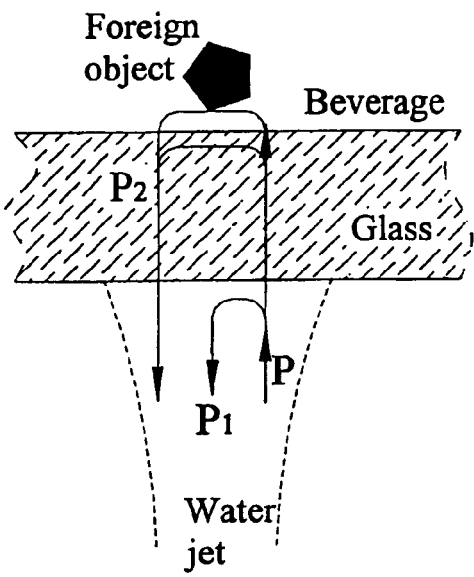
FIG. 3A   FIG. 3B
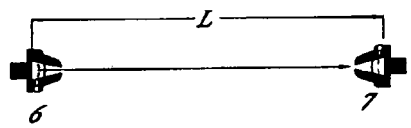
FIG. 4A
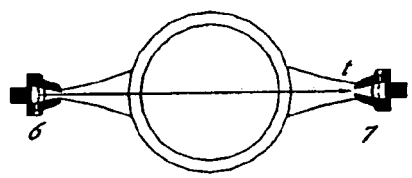
FIG. 4B
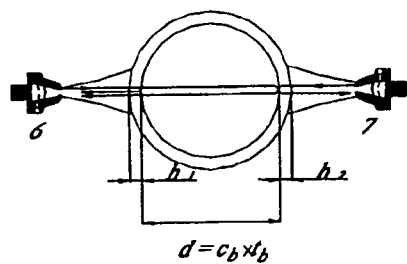
FIG. 4C

REAL-TIME SYSTEM FOR DETECTING FOREIGN BODIES IN FOOD CONTAINERS USING ULTRASOUND

RELATED APPLICATIONS

This application is a divisional of U.S. Ser. No. 10/889,444, filed Jul. 12, 2004 now U.S. Pat. No. 6,993,972, which is a divisional of U.S. Ser. No. 10/263,383 filed Oct. 2, 2002 now U.S. Pat. No. 6,782,752, which claims priority to U.S. Provisional Application Ser. No. 60/326,547, filed Oct. 2, 2001.

FIELD OF THE INVENTION

The present invention relates to a container inspection system using ultrasonic technique for two objectives (1) on-line detect and inspect foreign objects in bottled beverages, and (2) on-line sort and classify the bottled beverage based on their viscosity measurement.

BACKGROUND OF THE INVENTION

'Foreign Objects' (FOs) refers to any unwanted object in beverage product. Detection of FOs in beverages plays an important role in security control and quality assurance of food products. When beverages are manufactured or packaged small foreign objects might end up in the product. Fragments of glass and metal scarf may be found in glass jars or cans. It is naturally desirable for beverage production that all FOs are found and removed before they reach the consumers.

Mechanical separation techniques have been used for many years for finding foreign objects in powdered and flowing products on the basis of size and weight. See e.g. A. J. Campbell, "Identification of Foreign Body Hazards and the Means for their Detection and Control," (Technical Bulletin No. 88, UK: Campden Food & Drink Research Association. 1992). This method is appropriate only before the beverage is packaged in bottles or containers. Optical techniques can be used for after container filling inspection, as described by T. Gomm and S. E. Price in U.S. Pat. No. 4,136,930 entitled "Method and apparatus for detecting foreign particles in full beverage containers" issued in 1979, and by P. Weathers in U.S. Pat. No. 2,427,319 entitled "Beverage inspection machine" issued in 1947, but they are limited to clear transparency beverage bottles. X-rays and magnetic resonance imaging (MRI) could be another options but they are expensive, safety uncertain and complicated methods. See e.g. B. Zhao, O. Basir and G. Mittal, "Prototype of Foreign Body Detector for Beverage Containers by Ultrasonic Technique," submitted to Food research international in 2002, and B. Zhao, O. Basir and G. Mittal, "Foreign Body Detection in Foods by Ultrasound Pulse/echo Method," submitted to International Journal of Food Science & Technology in 2001.

Low intensity ultrasonic techniques can be used in beverage inspection because of their large applicability, reliability, safety and low cost. Nevertheless, there are only a limited number of publications related to packaged food inspections. For example, "Container inspecting apparatus," described by K. Tadahisa, K. Kunihiko, M. Yasuo and N. Masaji in E.P. Pat. No. 0821230 issued in 1998, which uses ultrasonic vibration to agitate effervescence of beverage from the bottom of the container to inspect the sealing performance.

The second publication is "Preliminary studies of a novel air—coupled ultrasonic inspection system for food containers" presented by T. H. Gan., D. A. Hutchines, and D. R. Billson, Journal of Food Engineering, vol. 53, pp 315–323 (2002) in which FO suspended in low density material container (soft drink bottle) was tested using air coupled transducers in thru-transmission mode.

Air coupled ultrasonic techniques have two drawbacks. One is that its application is limited to low density material due to the reflection of most of the transmitted energy because of acoustic impedance mismatch. The second is that this technique works in mode of separate transmitter and receiver. This mode is employed for either thru-transmission or surface wave detection. Thru-transmission is not a good mode for inspecting FOs sediment at the bottle bottom because the ultrasound signal can not transmit from the transmitter to receiver when they are separately placed under the bottom and above the top of the bottle being inspected. This is due to the bottle neck which shields the ultrasonic longitudinal transmission from bottom to cover. Surface wave technique detects flaws in a material by examining the time of flight of a pulse with respect to that of a back wall echo (inner surface of the container wall). This method is not suitable for detecting FOs inside a container since the presence of FOs does not change the time of flight from the inner surface of the bottle wall.

Water coupling can be used in high density container materials inspection. See. e.g. E. Haeggestrom, and M. Luukkala, "Ultrasound Detection and Identification of Foreign Bodies in Food Products", Food Control, vol. 12, p37 (2001), and M. Hiroshi, I. Sigeki, K. Tsukio, and N. Masanori in K. R Pat. NO. 9,005,245, entitled "Inspection method and apparatus for wrapped contents by ultrasonic," which is issued in 1990. however, in both of the publications the water tank immersion mode are used, which is not suitable for bottled beverage production on-line inspection because of its low inspection speed. See e.g. Y. Jiang, B. Zhao, O. Basir and G. Mittal, "LabView Implementation of an Ultrasound System for Foreign Body Detection in Food Products," submitted to Computers and Electronics in Agriculture in 2002.

In summary of the above-published ultrasonic techniques for food inspection, a fatal drawback is that they use point-detection (using one transducer or one pair of transducers). Only one small point of food container can be inspected each time by one transducer or transducer pair, which cannot catch up with the high speed food production. Their methods are therefore not suitable for on-line FOs inspection Product rating is another point for manufactures to optimize their pricing and sale strategy. Viscosity is one of indices for product quality rating which can indicate the juice concentration, mouth feel, the ingredient functionality, and shelf life. Conventional liquid viscosity measurement is conducted by Couette, plate-and-cone rotational, and parallel plate rheometers based on Poiseuille or Couette flow or oscillating flow. A drawback of these conventional methods is that they are normally conducted off-line. This makes it difficult to monitor product quality in real-time. Especially, this off-line inspection is an open-bottle percentage sampling method, i.e., one judges the quality of a bench of production based on the examination of one or two samples. The beverage quality in each individual closed bottle is different from each other but in fact is not known. Therefore, the quality of an individual bottle may be over-evaluated by the bench evaluation, which damages the reputation of the producer when it reaches consumers. In the opposite case, the producer loses money if the quality is under-evaluated by the bench evaluation.

Being rapid, non-destructive and non-invasive, ultrasonic technique is a promising approach for viscosity on-line measurement in food processing industry. Using ultrasonic technique the viscosity measurement can be approached by establishing a correlation between the viscosity of beverages and other measured physical properties of the ultrasound signal. R. Saggin, and J. N. Couplant described an ultrasonic reflectance coefficient method in "Ultrasonic characterization of oil viscosity and solids content" (2000 IFT Annual Meeting, Dallas, Tex. Jun. 11–14, 2000; 30D-11). An advantage of this method is that it only requires the reflection signal at one interface. However, this technique employs both amplitude and phase information at several frequencies to determined the viscosity. This makes the viscosity computation process relatively complicated. Furthermore, computing phase response in the spectrum is less accurate than that of computing amplitude response. M. J. McCarthy, R. L. Powell, J. A. Fort, D. M. Pfund, and D. M. Sheen presented ultrasonic Doppler velocimetry for food viscosity measurement, "Development of ultrasonic Doppler velocimetry for viscosity measurements" (2000 IFT Annual Meeting. Dallas, Tex. Jun. 11–14, 2000 nr 49-6). They used ultrasonic Doppler Velocimetry to determine the velocity profile in a tube. This technique needs not only an accurate velocity measurement, but also an accurate spatial measurement and subsequent data fitting for the profile. See e.g. B. Zhao, O. Basir and G. Mittal, "Correlation Analysis between Beverage Viscosity and Sound Velocity," submitted to International Journal of Food Properties in 2002.

Velocity measurement by pulse/echo method is the simplest, widely used, and probably the most accurate in ultrasonic techniques. Using velocity of sound as a measure of beverage viscosity requires a governing law to predict how the viscosity is correlated with the ultrasound velocity. However, there is no direct or explicit correlation between the viscosity and the velocity of sound. Furthermore, using time-of-flight measurement to correlate the fluid viscosity is normally performed in a conduit of volume flow, as described by M. Guitis in D.E. Pat. No. 19940192, entitled "Device for determination of fluid parameters and fluid composition control based on on-line measurement of such fluid parameters using twin ultrasonic transducer and reflector arrays for accurate measurement of fluid parameters," which is issued in 2001. The viscosity obtained by this way is not the viscosity in each individual bottle. The time-of-flight in that patent is measured in such a way that the transmitter and receiver or reflector are well aligned and their distance is fixed. These conditions, good alignment and fixed distance, are not available for a beverage bottle: curvature of bottle surface demands a strict alignment, perception of as small as 1% variation of sound speed in beverages needs to on-line measure the real bottle diameter and wall thickness of each sample instead of using the nominal thickness.

SUMMARY OF THE INVENTION

Therefore, first object of the present invention is to provide a container inspecting apparatus and method which can on-line detect the FOs contained in bottles of materials of both low and high density, and both transparent and opaque, with high inspection speed, safety and low cost. Further object is to realize automatically on-line sorting or classifying filled bottles based on their quality index, i.e., viscosity correlated with ultrasound velocity measurement.

The present invention provides an apparatus for inspecting the foreign objects packed in beverage bottles, comprising: a transporting means, an ultrasonic transducer array disposed in the conveyor gap and underneath the conveyor level, a linear water jet nozzle accommodating the ultrasonic transducer array, a multi-channel pulse/receiver board to produce and receive ultrasonic pulse signals, two ultrasonic transducers placed separately on each side of conveyor, two round water jet nozzles, a two-channel pulse/echo board, and a computer to control the multi-channel pulse/receiver board and process the signals.

With the above arrangement, beverage bottles are transported onto the first conveyor after filling. The first conveyor moves forward the bottles to pass by the inspection gap where the ultrasonic transducer array transmits an ultrasound pulse and receives echo signals. The ultrasound pulse is transmitted to the bottom of the bottle via water jet coupling. The ultrasound transducer array is set on by a pulse/receiver board controlled by a computer. Echo signals are processed by computer by examining both the time of flight and the amplitude of the pulse. Bottles are deviated out of the production line if FOs are detected. Bottles without FOs continue moving forward and passing by viscosity test station formed by two face-to-face placed on each side of the conveyor. The ultrasound velocity in the beverage in the bottle is accurately measured by the two transducers taking into account of the bottle diameter and wall thickness. Viscosity of beverage inside the bottle is evaluated by correlation between the ultrasound velocity and the viscosity.

BRIEF DESCRIPTION OF THE DRAWINGS

FIG. 3A shows ultrasonic scanning on the bottle bottom with no foreign object present. FIG. 3B shows ultrasonic scanning on the bottle bottom with a foreign object present.

FIGS. 4A, 4B and 4C are schematics of ultrasonic echoes from outer and inner surfaces of glass bottle bottom in absence and presence of foreign object.

DETAILED DESCRIPTION OF THE INVENTION

Figure 1:
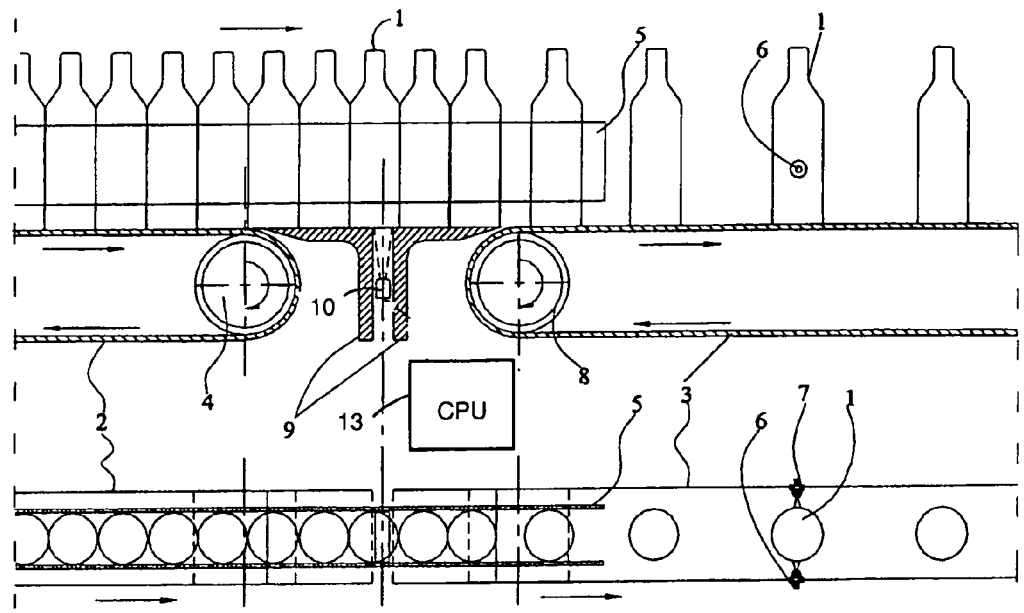
FIG. 1 is front and top views of a container inspecting and quality sorting apparatus.

As shown in FIG. 1, the beverage bottle inspection system includes two subsystems. The first subsystem is the container foreign object inspecting apparatus which comprises an ultrasound transducer array in conjunction with a linear water jet nozzle, two conveyors and the lateral barrier accordingly. The second subsystem consists of two transducers, circular water jet nozzles and a two-channel pulse/echo board with high speed mode switching.

Figure 2:
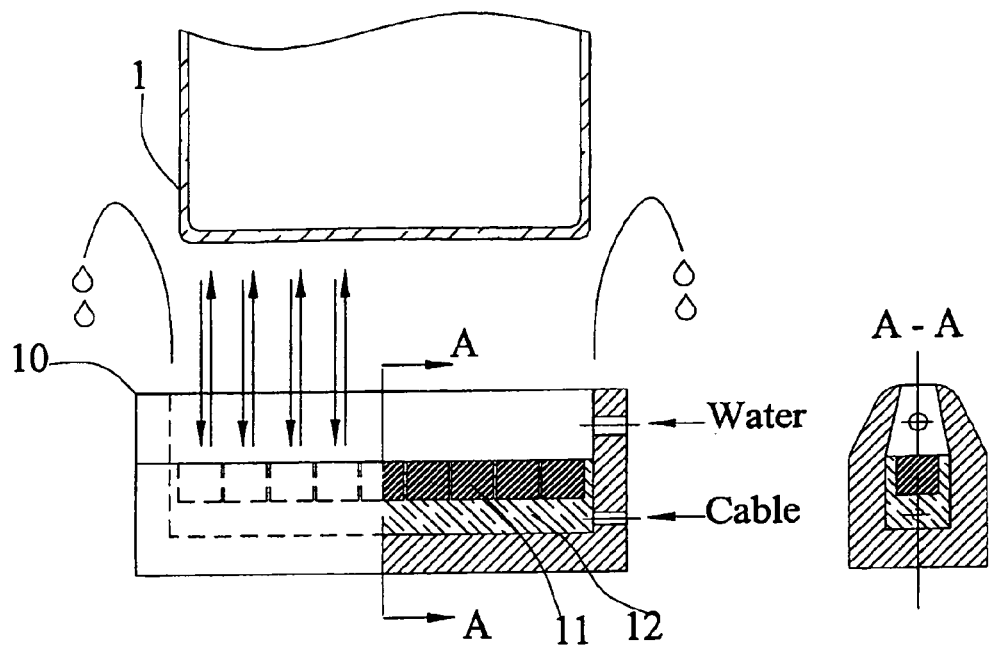
FIG. 2 is front and cross section views of water jet nozzle and ultrasound transducer array.

The bottles 1 after filling are transported by conveyor belt 2 and wheels 4 to the flat stage 9. Bottles 1 on stage 9 are then pushed by bottles behind to pass by the gap between the two flat stages 9. Barrier 5 is designed to keep the bottle straight-moving and prevent the bottle from falling down. Simultaneously, water is projected upward to the bottle bottom from the linear nozzle-house 10 sitting in the gap. Ultrasound pulse is produced by transducer array 11 and transmitted through water jet to the bottle bottom shown in FIG. 2. Array base 12 is used to support the array elements 10 and to transfer the echo signals to pulse/receiver board piloted by a computer 13. The computer 13 includes a processor, memory, hard drive and any other necessary hardware to control and receive data from the transducer array 11 and transducers 6 and 7. The computer 13 is suitably programmed to perform the data analysis described below.

Two echo signals respectively from outer and inner surfaces of the container bottom are examined for their amplitudes which depend on the impedances on the interface of two materials, i.e., water/bottom and bottom/beverage. These two echo signals are represented by $P_1$ and $P_2$ respectively for outer and inner surfaces of the bottle bottom shown in FIG. 3.

In absence of FOs, the two reflections pressure ratio is calculated by:

$$\frac{P_2}{P_1} = \frac{4Z_w Z_m}{(Z_w + Z_m)} \cdot \frac{(Z_b - Z_m) \cdot e^{-\alpha h}}{(Z_b + Z_m)(Z_m - Z_w)} \quad (1)$$

where $Z_w$, $Z_m$, $Z_b$ are respectively the acoustic impedance of water, container material, and the beverage. $\alpha$ and h are respectively the acoustic attenuation coefficient of the container material and the thickness of the container bottom.

The pressure ratio $P_2/P_1$ is changed in presence of foreign objects in the container bottom due to the superimposition of the reflection of the foreign object to $P_2$ as shown in FIG. 4. The change of pressure ratio $P_2/P_1$ is used as criteria for inspecting FOs.

From a theoretical standpoint, the presence of FOs can be detected by measuring the pressure amplitude of the second reflection; given that the incident pressure P is shown in FIG. 3. However, the incident pressure in many cases is unknown as it represents the pressure just before impacting the container. This pressure can be estimated based on the pressure propagation from the transducer through the delay line, to the nozzle, and finally to the outlet of the nozzle. This calculation is inaccurate due to signal attenuation, complexity of the geometry of the nozzle, instability of transducer driving voltage, and variations in the gap between the nozzle and the container bottom due to container surface irregularity. All these factors may lead to false FO detection. In contrast, the pressure ratio between $P_2$ and $P_1$ is immune to such anomaly since the above variations vanish as a result of the division operation ($P_1$ and $P_2$ are both proportional to the incident pressure and are subject to the same uncertainties).

It may also be noted that Equation (1) seems independent of frequency, as there is no explicit frequency terms in these equations. However, this is not the case. The frequency dependence comes from pressure values which are derived from the frequency spectrum of the reflections. In order to enhance the signal to noise ratio to obtain accurate signal peak values from the spectrum an algorithm for signal selection and separation is needed. Signal selection and separations is not an issue if the bottom is thick enough (time-of-flight of pulse in the container bottom is much larger than the pulse duration). One can readily separate two echoes signals and perform spectrum calculation of each echo by augmenting the rest of the signal by zeros in this case. If the bottom is not thick enough, which may happen to many practical applications, it is difficult to determine where to separate the two close placed or even overlapped signals, because small shift for separation point may lead to big difference in spectrum calculation result. To overcome this problem an algorithm of time-frequency analysis (windowed short time Fourier transform) was developed. In this algorithm a sliding window of width N was used to chop the sampled signal. A Fast Fourier Transform (FFT) was applied to these N points to determine the amplitude of the pulse center frequency. The window was then moved forward one point along the signal to perform the same operation. Repeating this process throughout the signal, the history of the pulse amplitude at center frequency was obtained. The two echoes appear as two separated peaks in the time history. In this method it does not need to subjectively determine the separation point for the two narrowly spaced echoes. The only thing to do is to slide the window and calculate the spectrum, which is especially suitable for computer programming.

The window width N was important for this technique. Large N has higher frequency resolution but poor time localization and small N has reverse consequence. In principle, the window width is so determined that 99% energy of the pulse is included. To minimize the impact of phase on the spectrum amplitude Hamming or Hanning rather than rectangular window is recommended to be employed prior to the FFT operation.

After going through the FOs detection, the viscosity of beverage in each bottle is evaluated passing by the viscosity test station. The ultrasound velocity $c_b$ in the beverage is calculated by $$c_b = \left( \frac{t}{t_b} - \frac{h_1 + h_2}{c_m t_b} - \frac{L - h_1 - h_2}{c_w t_b} - 1 \right) \cdot c_w \quad (2)$$

where, as shown in FIG. 4, L is the distance between the two transducers, $c_w$ and $c_m$ are sound velocities for water and the bottle material, $h_1$ and $h_2$ are thickness of the bottle wall close respectively to transducers 6 and 7, t is the traveling time of pulse from transducer 6 to 7 when the bottle is situated in the pulse path, $t_b$ is the traveling time of echoes between the two inner walls.

Sound velocity of the beverage $c_b$ is measured in the following procedure. The two aligned transducers 6 and 7 are first set to thru-transmission mode to get the traveling time t when the bottle is situated in the ultrasound beam path between the two transducers. Then the two transducers are switched to pulse/echo mode to measure the time of flight of echoes between the inner and outer surfaces of the bottle walls close respectively to the two transducers. The thickness $h_1$ and $h_2$ are equal to the sound velocity in the bottle material multiplied respectively by the time of flight in each side. The ultrasound propagation time $t_b$ in beverage in the bottle of inner diameter d is the time difference between the second and third echoes obtained in pulse/echo mode.

A key technique in the sound velocity measurement in the above procedure is that the measurement should be performed when the bottle is well aligned with the two transducers. For a circular cross section bottle this means that the ultrasound beam emitted by the transducer is normal to the surface of the bottle. A simple way to detect if the bottle is in good alignment with the two transducers is to check the amplitude of the echo from the outer surface of the bottle. When the bottle is well aligned with two transducers, the echo amplitude of the outer surface of the bottle should be the maximum. This method was used to determine the normal to the skin for automated meat grading by ultrasound sensors, and claimed by A. A. Goldenberg, N. Kircanski, and Z. Lu in U.S. Pat. No. 6,322,508, entitled "Automated meat grading method and apparatus" issued in 2001. However, maximum-echo amplitude is not always a reliable criteria for the normal searching. For example, the driving voltage fluctuation and the distance variation between the water jet nozzle and the target can lead to an error determination in the normal searching. In the present invention, a frequency shift criteria is used to judge the alignment of the bottle. In this method, the spectrum of the outer surface echo is calculated and the frequency of the maximum amplitude is therefore examined. For a given transducer the frequency of the maximum amplitude in the spectrum is called nominal center frequency and provided by the manufacture, which is determined by an experiment orienting the transducer normal to the surface of the object. The frequency of the maximum amplitude in spectrum of the echo signal is lower than the nominal frequency if the transducer is not normal to the object surface. Since this criteria used in the present invention is the frequency shift of the maximum amplitude instead of maximum amplitude in the spectrum, this method is immune to uncertainties due to the driving voltage and distance changing produced amplitude fluctuation.

In the course of inspection, the transducer 6 is set to pulse/echo mode to continuously examine the frequency of maximum amplitude in the spectrum of outer surface echo. As soon as the center frequency of the transducer is reached, the transducers 6 and 7 are first switch to thru-transmission mode to measure the traveling time t and then both to pulse/echo mode to measure thickness $h_1$, $h_2$ and traveling time $t_b$ as explained in the above.

The following examples illustrate the principles applied to the inspection system of the present invention.

EXAMPLE 1

Bottom Scanning for Foreign Object Detection and Tomograph.

Figure 5:
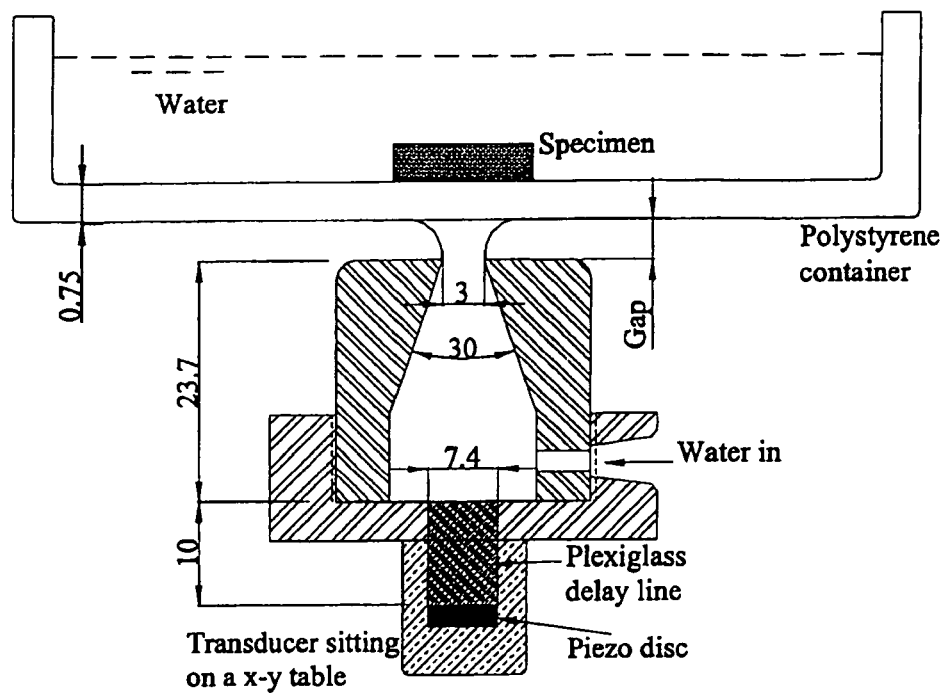
FIG. 5 is a schematic of single ultrasonic transducer scanning a bottle bottom.

The experimental set-up of the prototype is shown in FIG. 5. A polystyrene container with flat bottom of thickness 0.75 mm was supported by a holder. An ultrasonic transducer with delay line is mounted on the bottom of a plexiglass water jet nozzle that is supplied with water by a flow controllable pump. The delay line is made of a plexiglass cylinder of 7.40 mm in diameter and 10 mm in length that produces a time delay of 7.6 μs. The nozzle has a 3 mm diameter at exit. The ultrasound pulse is transmitted to the bottom of the polystyrene container through the water jet. The ultrasound signal traveling distance is 23.70 mm from the delay line to the exit of the nozzle. A 2 mm gap is kept between the container bottom and the nozzle tip so that the transducer sitting on the x-y table can scan the container bottom smoothly. The water flow is controlled at a rate of 40 liters per hour.

The transducer used was a flat-focused ultrasonic transducer of center frequency 4 MHz. The ultrasonic pulse was coupled to the water by delay line. A SR-9000 Pulse/Receiver card was used to drive the transducer and to receive the echo signal. Pulses were produced by SR-9000 at a repetition rate of 2 kHz. The signal sampling frequency was 100 MHz.

Tap water was used for both the water jet and in the container. Five specimens: plexiglass, glass, aluminum stainless steel and copper, were tested. All these specimens were cut into pieces of 10 mm in square whose acoustic parameters are listed in Table 1.

A Labview 5.0 program was composed to control the SR-9000 card and the x-y table, and to process the echo signals simultaneously. The result was displayed on the monitor in real time.

TABLE 1

| Acoustic impedance for materials used in experiment | |
|---|---|
| Material | Impedance [kg/m²s] |
| Polystyrene | $2.47 \times 10^6$ |
| Plexiglass | $3.16 \times 10^6$ |
| Glass | $12.3 \times 10^6$ |
| Aluminum | $17 \times 10^6$ |
| Stainless steel | $45.45 \times 10^6$ |
| Copper | $41.61 \times 10^6$ |
| Water | $1.48 \times 10^6$ |

Figure 6:
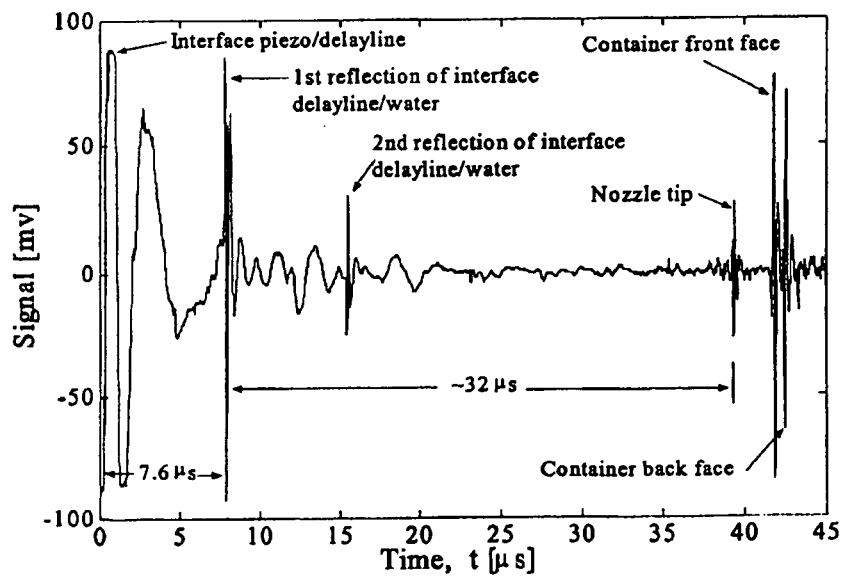
FIG. 6 shows ultrasonic signal propagation in the system of FIG. 5.

FIG. 6 is a signal from the container without specimen presence. In this figure, the echo timing is shown from the interface of piezo/plexiglass delay line to the interface of water jet/back face of container, where 7.6 μs is the round trip time of ultrasound in the delay line, 32 μs is that of water in the nozzle. The 32 μs delayed tip pulse is due to the discontinuity of tip boundary. After the reflection on the interface of delay line/water, a pulse was observed which is the second reflection on the same interface. Some noise before the container outer surface reflection time could come from shear wave of the delay line. The reflections from front and back faces are after the nozzle tip pulse, which happens at approximately after 42 μs.

Figure 7:
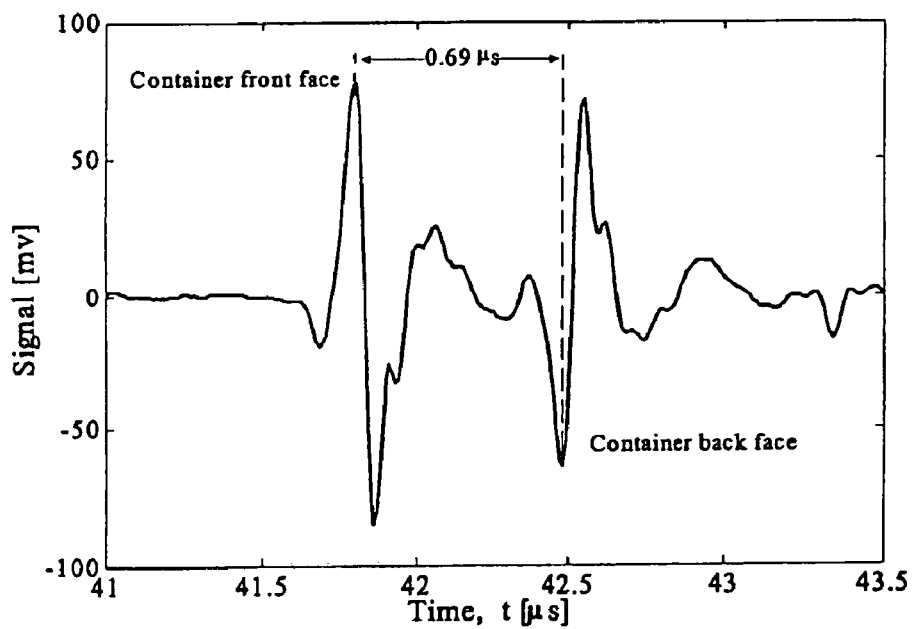
FIG. 7 is a zoomed picture for FIG. 6 around 42 µs, demonstrating overlapped echoes from outer and inner surfaces of bottle bottom.

FIG. 7 is the zoomed picture of two echoes from outer and inner surface of the bottom. It can be seen that the two echoes are overlapped and difficult to separate for performing spectrum calculation for each echo.

Figure 8:
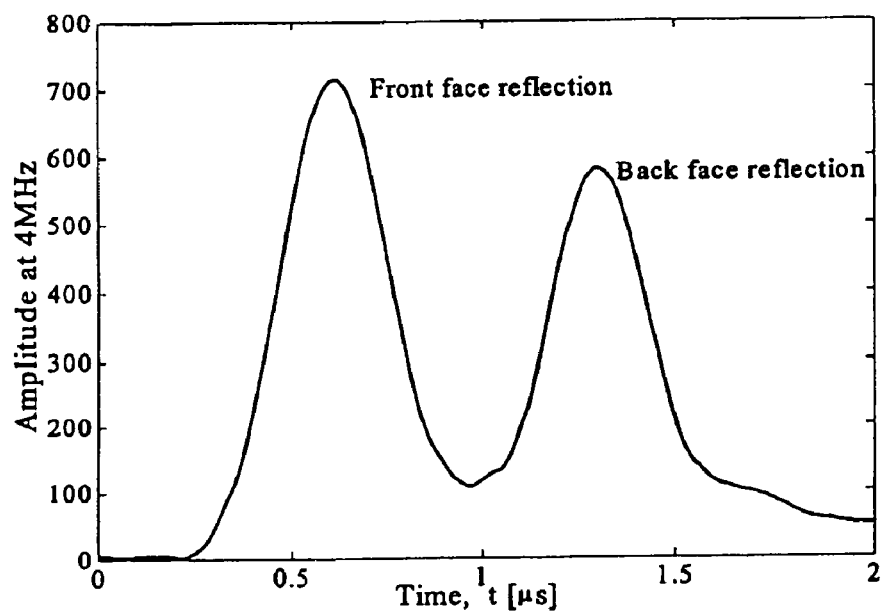
FIG. 8 is the center nominal frequency amplitude history calculated by using short time Fourier transform for the signal shown in FIG. 7.

FIG. 8 is the time history of the amplitude at center frequency of 4 MHz for the signal of FIG. 7 by using the "slide window" technique. The first peak is the amplitude of reflection of front face and the second peak is that of back face. The time difference between two reflections stays unchanged equal to that for the real time signal, but the peaks were easy to be sorted out and the pressure ratio $P_2/P_1$ is readily calculated.

Table 2 is a summary of using pressure ratio method to detect foreign objects of different materials. The results show that pressure ratio $P_2/P_1$ has significant changes from no-FO in presence of foreign object. This change heavily relies on the impedance difference: the bigger the impedance difference between the FO and the container, the larger the pressure ratio difference.

TABLE 2

Experimental results and comparison with theoretical predictions

| Material | Measured $P_2/P_1$ |
|---|---|
| No FO in container | 0.91 ± 0.03 |
| Plexiglass piece in container | 1.23 ± 0.01 |
| Glass piece in container | 2.85 ± 0.03 |
| Aluminum piece in container | 2.99 ± 0.08 |
| Copper piece in container | 3.29 ± 0.29 |
| Stainless steel piece in container | 3.28 ± 0.07 |

Using the slide window method and the pressure ratio criterion, specimen of glass in the container was inspected. It was found that the specimen can be detected as small as 2.5×2.5 mm square which is smaller than the nozzle cross section area.

Figure 9:
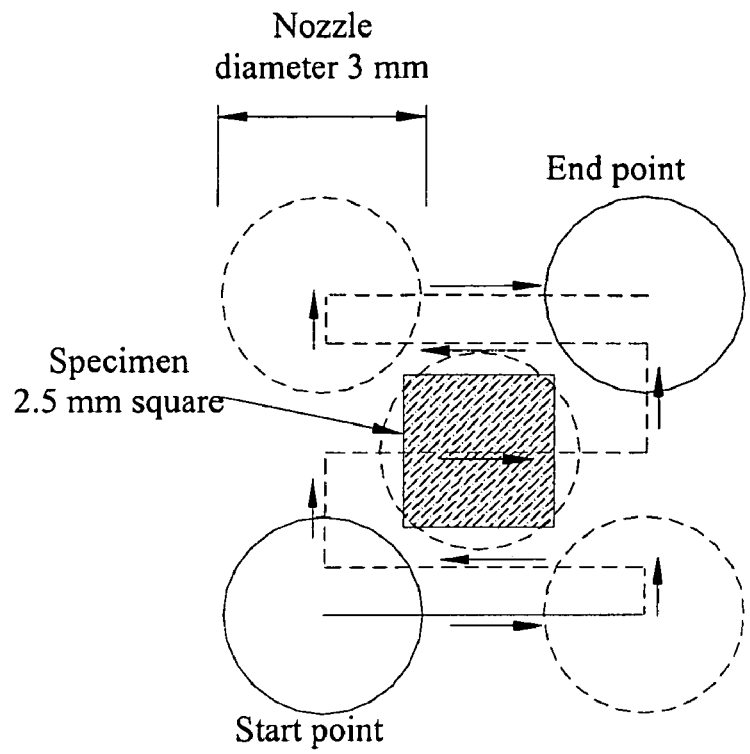
FIG. 9 is a scanning path of single ultrasonic transducer shown in FIG. 5 for foreign object detection.

FIG. 9 is a schematic of FBs detection by using ultrasonic beam scanning with x-y table. By this way the FBs' size can be estimated by directly reading the distribution of reflections pressure ratio.

Figure 10:
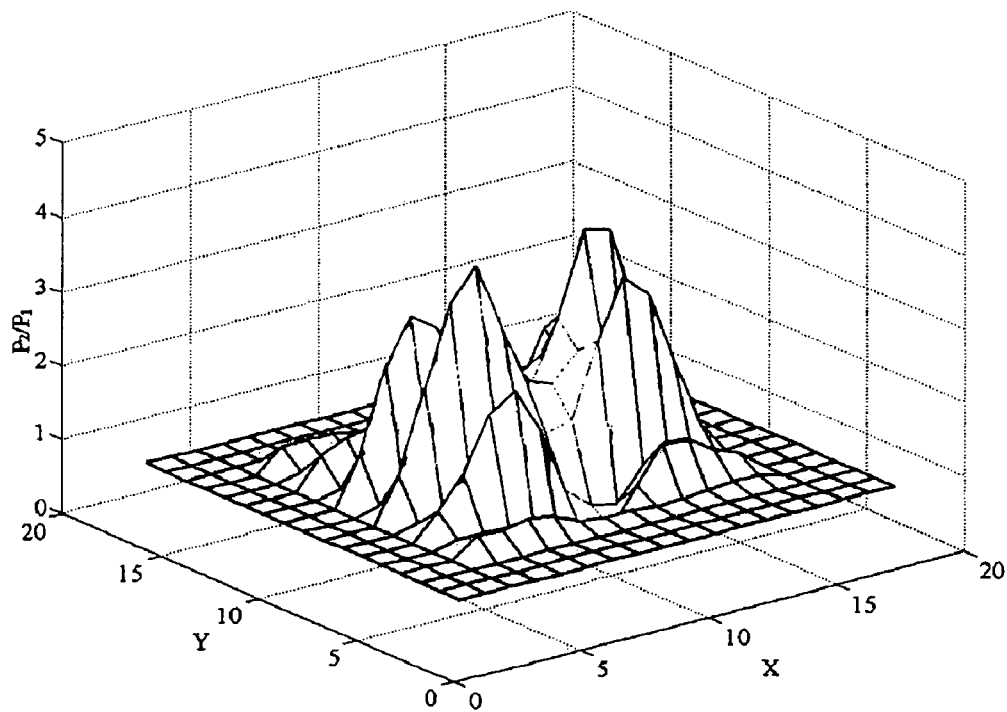
FIG. 10 is a tomograph of a glass fragment sediments on the bottom of the container scanned by the device as shown in FIG. 5.

FIG. 10 is a pressure ratio distribution of a glass specimen of 2.5×2.5 mm. The resolution of x-y table is 0.025 mm. The scale in the figure is 0.25 mm per division. A matrix of 17×18 for pressure ratio is obtained for 17 line scanning with 18 measurement on each. Roughly the amplitude ratio is larger when the transducer is right underneath the specimen than far away from the specimen. The space between two peaks is 5 divisions corresponding to 2.5 mm of the specimen size. However, the maximum amplitude did not occur in the center position. The reasons was that ultrasound beam was not perfectly perpendicular to the front face at that moment due to loosening produced tilting of the nozzle in course of x-y table movement. This phenomenon did not come out again after fixing the nozzle. This phenomenon also indicates the importance of good alignment in ultrasonic measurement.

Summary

The above example shows that the foreign objects on the bottom of container can be detected and localized by the present invention examining the pressure ratio between the inner and outer surface of the bottom, which is immune to the instability of driving voltage and the distance fluctuation between the transducer and the container bottom. Using of windowed short time Fourier transform can improve the speed of echo signal recognition and are therefore suitable for rapid real time inspection in production lines.

EXAMPLE 2

Figure 11:
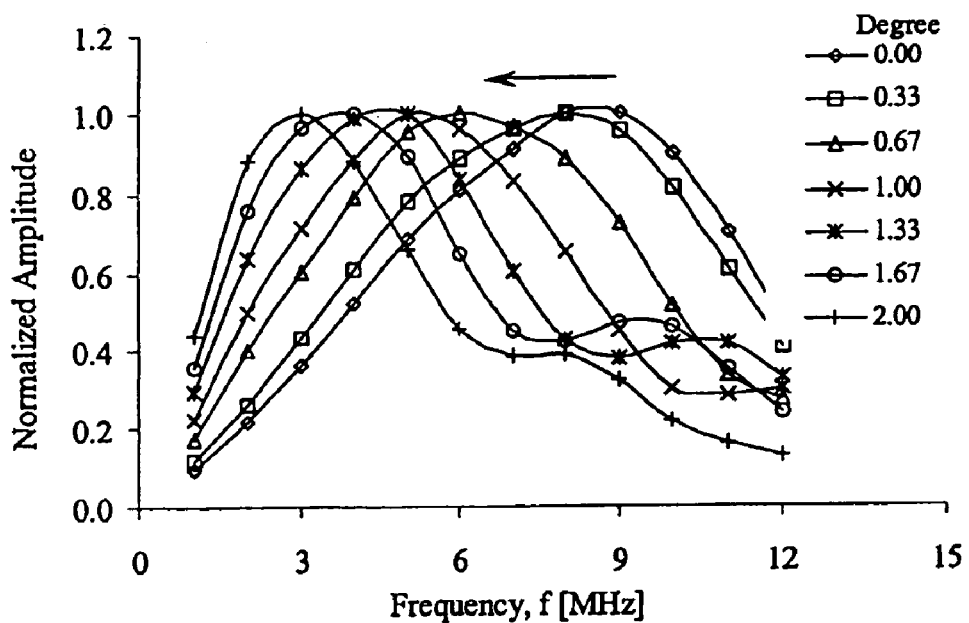
FIG. 11 is the normalized spectrum of echo signal from outer surface of Plexiglas plate of 4.40 mm thick. The frequency of the maximum amplitude shifts to lower side as the incident angle increases.
Figure 12:
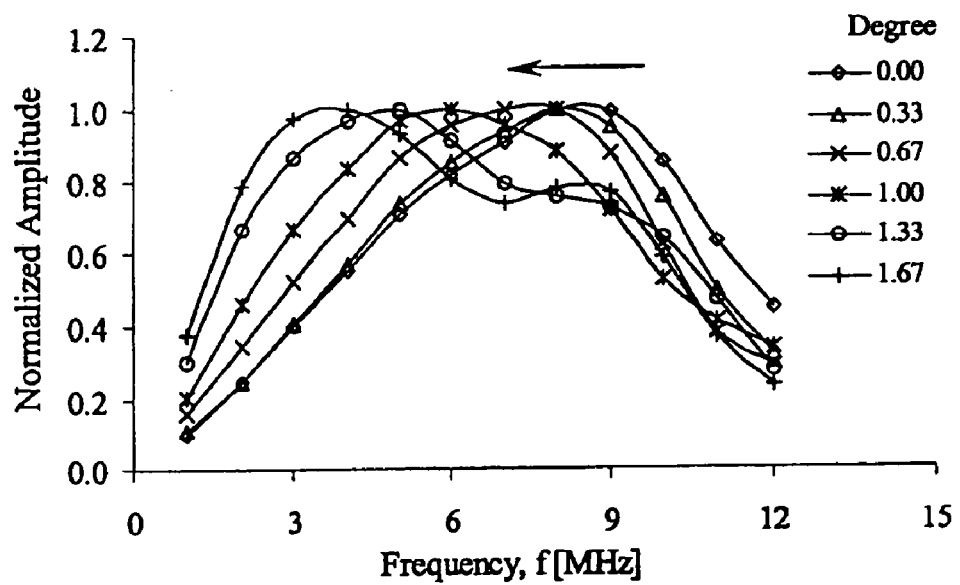
FIG. 12 is the normalized spectrum of echo signal from outer surface of glass plate of 2.67 mm thick. The frequency of the maximum amplitude shifts to lower side as the incident angle increases.

Automatic sensing for the bottle alignment using nominal center frequency shift principle: Using a transducer of nominal center frequency of 8.5 Mhz and the same pulse/receiver card as in example 1 the nominal frequency was investigated by changing the incident angle of the transducer to the object being inspected. In this experiment, the transducer/nozzle was mounted on a rotary stage of angular resolution 0.16 degree. The experiment was started by orienting the nozzle at right angle to object being inspected. Then the rotary stage was rotated clockwisely and counterwisely to 2° with increment of 0.33°. The reflected signals were sampled for every rotation of the stage. 100 signals were sampled for each angle and averaged. The amplitudes spectrum were normalized by the maximum amplitude of each spectrum. Different amplitude of echo signals was obtained using Plexiglas and glass plate because their big difference in acoustic impedance. The result is presented in FIGS. 11 and 12 for spectrum of echoes from Plexiglas and glass sample. The frequency of the maximum amplitude in the spectrum shifts to lower side in both cases as the incident angle increases. Although the reflection amplitude of glass is 2.4 times greater than that of the Plexiglas the normalized spectrum and the frequency shift is identical for both samples.

By this method the frequency of maximum amplitude is confirmed as 8.5 MHz for the given transducer at the right angle incident. The figures also show the high sensitivity of this method for the normal tracking of a surface: the maximum amplitude frequency changes from 8.5 to 3 MHz when the incident angle varies from zero to two degree, which is preferred for rapid alignment determination in production line.

EXAMPLE 3

Ultrasound Velocity and Viscosity Measurement for Bottled Beverage and their Correlations.

Using the auto localization technique described in example 2 and based on equation (2) the ultrasound velocities in juices were measured. Juices were contained in a glass bottle of 41.63 mm nominal outer diameter and 1.55 mm wall thickness. Orange juice without pulp, tomato juice, and suspension of RC/CL were used in the tests. The RC/CL is a co-processed blend of cellulose gel (microcrystalline cellulose) and cellulose gum (sodium carboxymethyl cellulose), used as an ingredient in food processing. Beverages of various qualities were obtained by adding dilution water in juices.

Figure 13A:
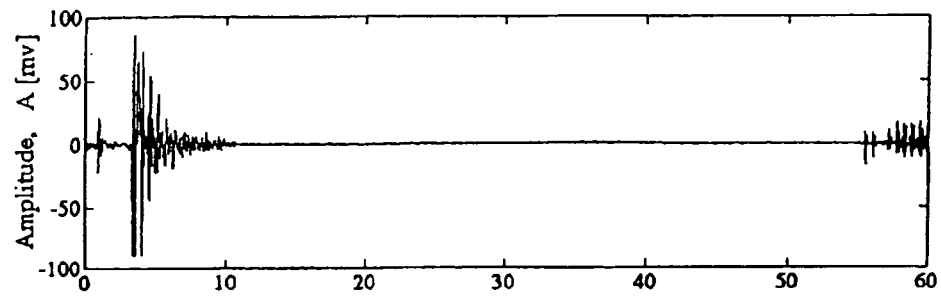
FIGS. 13A and 13B illustrate a time history of center frequency amplitude calculated by windowed short time Fourier transform for a real time echo signal propagated in orange juice filled in a glass bottle.
Figure 13B:
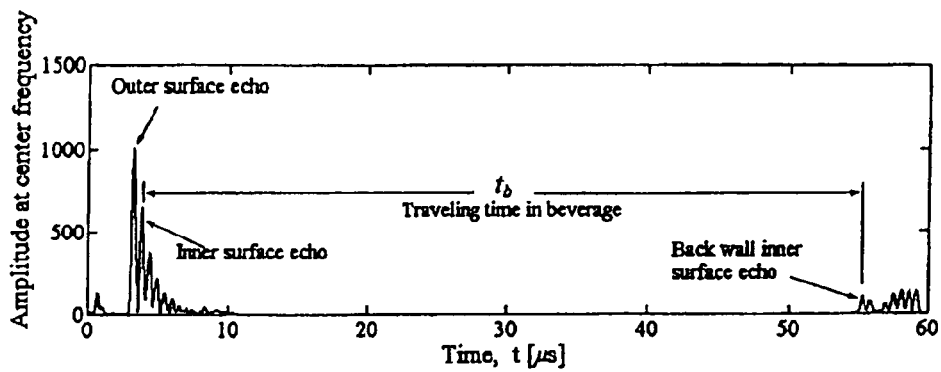

FIG. 13 is the real time signal of orange juice sampled by transducer 6 using pulse/echo mode and the time history of the amplitude at center frequency in spectrum obtained by using slide window. The thickness $h_1$ is calculated by the time difference between the echoes from the outer and inner surfaces of the bottle shown in the figure. The thickness $h_2$ is obtained by transducer 7 in the same way. Propagation time $t_b$ in the beverage is calculated by the difference between the two inner wall surfaces, which are the second and the third peaks after the outer surface peak in FIG. 13.

Viscosities of beverages were measured at shear rate of 10.47 rad/s by a concentric rotational viscometer. Diameters of the two cylinder are respectively 56.20 and 103.20 mm. Samples' temperature was controlled to within 20±0.28° C.

Figure 14:
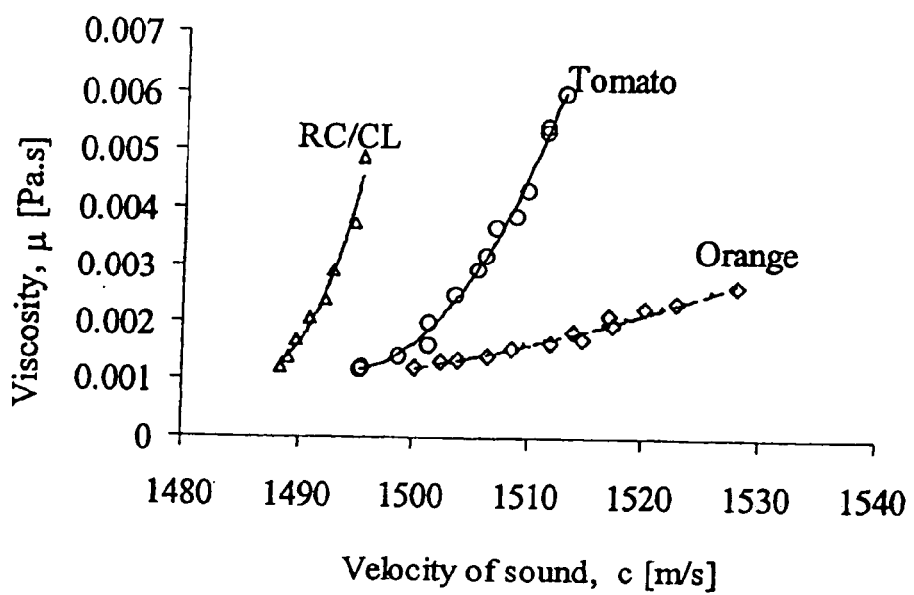
FIG. 14 is the results of viscosities of juices and suspension as a function of the ultrasound velocity.

FIG. 14 shows the experimental results of viscosity and velocity of sound measured for tomato and orange juices and RC/CL suspension. The round, diamond and triangle points in the figure are experimental data. The velocity of sound in tomato juice is found in agreement in range with published data. See e.g., R. Saggin, and J. N. Couplant, "Concentration measurement by acoustic reflectance," J Food Sci., vol. 66, pp. 681–685 (2001). It was not found pertinent velocity data of orange juice for comparison with our experimental results. The solid and dashed lines in the figure are correlation between the viscosity μ and ultrasound velocity $c_b$, which is best represented by a quadratic relation (3).

$$\mu = a_2 c_b^2 + a_1 c_b + a_0 \quad (3)$$

Table 3 contains coefficients for Equation (3) for two juices with coefficient ($R^2$). It is demonstrated that the viscosity of beverages is highly quadratically correlated with the velocity of sound. This relationship can be used in the bottled beverages viscosity on-line test. Correlation coefficients $a_0$, $a_1$ and $a_2$ are different depending on the juice to be inspected.

TABLE 3

Coefficients for Equation (3) with coefficients ($R^2$) of determination

|  | $a_2$ | $a_1$ | $a_0$ | $R^2$ |
|---|---|---|---|---|
| Tomato Juice | $10 \times 10^{-6}$ | −0.0422 | 31.552 | 0.9927 |
| Orange Juice | $0.7 \times 10^{-6}$ | −0.0021 | 1.565 | 0.9732 |
| RC/CL suspension | $50 \times 10^{-6}$ | −0.1553 | 115.52 | 0.9740 |

We claim:

1. A method for determining a viscosity of a fluid within a container including the steps of:
   a) positioning the container between a pair of transducers;
   b) measuring a through-transmission time through the container and fluid between the transducers;
   c) measuring an outer echo transmission time of an outer echo signal from an outer surface of the container and an inner echo transmission time of an inner echo signal from an inner surface of the container;
   d) determining a time difference between the outer echo transmission time and the inner surface transmission time;
   e) determining a viscosity $c_b$ of the fluid based upon said steps b)–d) as:

$$c_b = \left( \frac{t}{t_b} - \frac{h_1 + h_2}{c_m t_b} - \frac{L - h_1 - h_2}{c_w t_b} - 1 \right) \cdot c_w$$

where, L is a distance between the pair of transducers, $c_w$ and $c_m$ are sound velocities for water and a material of the container, $h_1$ and $h_2$ are the thicknesses of the container wall close to each of the pair of transducers, t is the through-transmission time, and $t_b$ is the traveling time of echoes between the two inner walls.

2. The method of claim 1 further including the step of:
   f) determining alignment between at least one of the pair of transducers and the container.

3. The method of claim 2 wherein said step f) is determined based upon an amplitude of an echo signal from the outer surface of the container.

4. A method for determining a viscosity of a fluid within a container including the steps of:
   a) positioning the container adjacent at least one transducer;
   b) determining alignment between the container and the at least one transducer
   c) measuring a through-transmission time through the container and fluid;
   d) measuring a thickness of a wall of the container between the at least one transducer and the fluid; and
   e) determining a viscosity $c_b$ of the fluid based upon said steps b)–d) as:

$$c_b = \left( \frac{t}{t_b} - \frac{h_1 + h_2}{c_m t_b} - \frac{L - h_1 - h_2}{c_w t_b} - 1 \right) \cdot c_w$$

where, L is a distance between the pair of transducers, $c_w$ and $c_m$ are sound velocities for water and a material of the container, $h_1$ and $h_2$ are the thicknesses of the container wall close to each of the pair of transducers, t is the through-transmission time, and $t_b$ is the traveling time of echoes between the two inner walls.

5. A system for determining a viscosity of a fluid in a container comprising:
   an ultrasonic transducer for generating an ultrasonic pulse into the container;
   a processor receiving signals from the transducer and determining a through-transmission time of the ultrasonic signal through a wall of a container within which the fluid is contained based upon the signals, the processor determining a through-transmission time of the ultrasonic pulse through the wall of the container and the fluid, the processor determining the viscosity $c_b$ of the fluid based upon the through-transmission time through the wall and the through-transmission time through the wall and the fluid as:

$$c_b = \left( \frac{t}{t_b} - \frac{h_1 + h_2}{c_m t_b} - \frac{L - h_1 - h_2}{c_w t_b} - 1 \right) \cdot c_w$$

where, L is a distance between the pair of transducers, $c_w$ and $c_m$ are sound velocities for water and a material of the container, $h_1$ and $h_2$ are the thicknesses of the container wall close to each of the pair of transducers, t is the through-transmission time, and $t_b$ is the traveling time of echoes between the two inner walls.

* * * * *